(12) United States Patent
Karedla et al.

(10) Patent No.: US 12,009,091 B2
(45) Date of Patent: Jun. 11, 2024

(54) PHARMACY SIG CODES AUTO-POPULATING SYSTEM

(71) Applicant: Walmart Apollo, LLC, Bentonville, AR (US)

(72) Inventors: Ravi Shankar Karedla, Bangalore (IN); Jingying Zhang, Beaumont, TX (US); Paridhi Kabra, Indore (IN); Shilka Roy, Noida (IN)

(73) Assignee: WALMART APOLLO, LLC, Bentonville, AR (US)

( * ) Notice: Subject to any disclaimer, the term of this patent is extended or adjusted under 35 U.S.C. 154(b) by 222 days.

(21) Appl. No.: 16/865,112

(22) Filed: May 1, 2020

(65) Prior Publication Data
US 2020/0350064 A1 Nov. 5, 2020

Related U.S. Application Data

(60) Provisional application No. 62/892,963, filed on Aug. 28, 2019.

(30) Foreign Application Priority Data

May 3, 2019 (IN) .............................. 201911017691

(51) Int. Cl.
| G16H 40/20 | (2018.01) |
| G06F 40/174 | (2020.01) |
| G06F 40/205 | (2020.01) |
| G06F 40/284 | (2020.01) |
| G06N 20/00 | (2019.01) |
| G16H 10/60 | (2018.01) |
| G16H 15/00 | (2018.01) |

(Continued)

(52) U.S. Cl.
CPC ........... *G16H 40/20* (2018.01); *G06F 40/174* (2020.01); *G06F 40/205* (2020.01); *G06F 40/284* (2020.01); *G06N 20/00* (2019.01); *G16H 10/60* (2018.01); *G16H 15/00* (2018.01); *G16H 20/10* (2018.01); *G16H 50/20* (2018.01); *G16H 50/70* (2018.01); *G16H 70/20* (2018.01)

(58) Field of Classification Search
CPC ........ G16H 20/10; G16H 20/00; G16H 15/00; G16H 10/00; G16H 10/60; G06F 40/205; G06F 40/174
See application file for complete search history.

(56) References Cited

U.S. PATENT DOCUMENTS

10,311,536 B1 * 6/2019 Ansari .................. G06Q 30/04
2006/0235881 A1 * 10/2006 Masarie ................ G06F 40/295
(Continued)

*Primary Examiner* — Samuel G Neway
(74) *Attorney, Agent, or Firm* — Fitch, Even, Tabin & Flannery LLP (57) ABSTRACT

Systems, methods, and computer-readable media are configured to auto-populate pharmacy SIG codes based on pattern matching model in a pharmacy system. The prescriptions including one or more fields of prescription information in natural language are received in the system. The prescription information can be parsed according to rule-based pattern matching model. The parsed prescription information can be mapped to a token SIG using rule-based pattern matching model dictionaries. A prescription SIG code based on each of the token SIG can be generated. A confidence value of the prescription SIG code based on character coverage of the prescription can be calculated.

21 Claims, 11 Drawing Sheets

(51) Int. Cl.
*G16H 20/10* (2018.01)
*G16H 50/20* (2018.01)
*G16H 50/70* (2018.01)
*G16H 70/20* (2018.01)

(56) References Cited

U.S. PATENT DOCUMENTS

| | | | |
|---|---|---|---|
| 2009/0099870 A1* | 4/2009 | Wilkinson | G06F 40/274 |
| | | | 705/3 |
| 2012/0290319 A1* | 11/2012 | Saria | G16H 15/00 |
| | | | 705/3 |
| 2013/0060793 A1* | 3/2013 | Bandyopadhyay | G16H 10/60 |
| | | | 707/755 |
| 2013/0085781 A1* | 4/2013 | Navani | G06Q 10/06 |
| | | | 705/3 |
| 2016/0110502 A1* | 4/2016 | Bronson | G16H 50/70 |
| | | | 705/3 |
| 2017/0068798 A1* | 3/2017 | Akinwale | G16H 70/40 |
| 2020/0350064 A1* | 11/2020 | Karedla | G16H 70/20 |

* cited by examiner

| Type | Number of eRXs ▷ | Percentage of Total eRXs ▷ | Percentage Of Auto-Populated eRXs ▷ |
|---|---|---|---|
| Total eRXs | 17500 | 100% | - |
| Auto-populated eRXs (Coverage) | 13674 | 78.1% | 100% |
| Auto-populated With 100% Confidence | 11028 | 63.0% | 81% |

Table I. Accuracy of converting prescriptions to SIG codes

| Confidence Bucket | Number Of SIG Codes | Percentage Of Total Autopopulated SIG |
|---|---|---|
| [0%, 20%] | 2 | 0.01% |
| [20%, 40%] | 31 | 0.23% |
| [40%, 60%] | 199 | 1.46% |
| [60%, 80%] | 1198 | 8.76% |
| [80%, 100%] | 1216 | 8.89% |
| 100% | 11028 | 80.65% |
| Total | 13674 | |

Table II. Confidence value distribution

FIG. 11

PHARMACY SIG CODES AUTO-POPULATING SYSTEM

RELATED APPLICATIONS

The present application claims priority to and the benefit of Indian Patent Application No. 201911017691, filed on May 3, 2019, and U.S. Provisional Application No. 62/892,963, filed on Aug. 28, 2019, the disclosures of which are incorporated by reference herein in their entirety.

BACKGROUND

In pharmacy system, after electronic prescriptions are received, relevant fields of prescription information are extracted by the system. Signature (SIG) Codes are short hand codes to input prescription directions efficiently. However, most of the SIG codes related to the electronic prescriptions need to be input manually.

DETAILED DESCRIPTION

Exemplary embodiments of the present disclosure are related to systems, methods, and computer-readable media configured to autonomously auto-populate prescription data with pharmacy SIG codes, which can be rendered in GUI, and calculate confidence values associated with the auto-populated SIG codes.

In accordance with embodiments of the present disclosure, in a pharmacy system, electronic prescriptions (eRX) are received as XML-files, which contain prescription information, such as patient name, drug name, prescriber name, and signature (i.e., patient instruction) in plain text. The patient instruction in a prescription can include six major components, Dosage, Frequency, Add-on, Route, Duration, Verb, and Medical Conditions. Exemplary embodiments can create dictionaries for each component to map patterns to the relevant SIG code. Regular expressions pattern matching can be used for mapping these dictionaries to the relevant SIG codes. Exemplary embodiments can construct similar patterns that can be used by the system to detect each of the components. To train the pattern matching model, a random set of prescriptions can be utilized as training data to build the dictionaries and rules. The SIG code for each prescription in the training data can be tokenized and/or normalized to serve as ground truth on which to build the model. Exemplary embodiments of the present disclosure can also provide a real-time accuracy measure of confidence of auto-populated pharmacy SIG codes.

Figure 1:
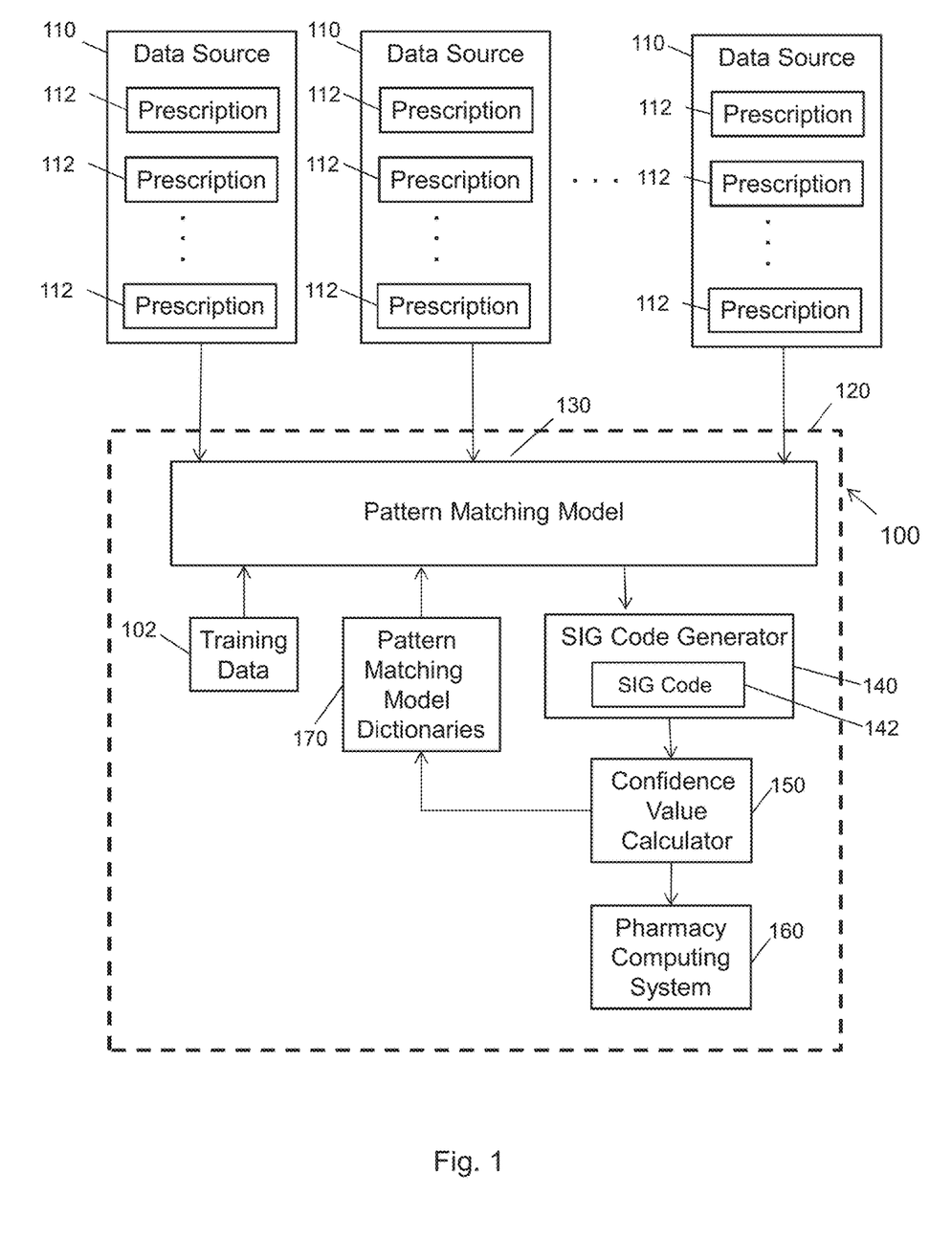
FIG. 1 is a block diagram of an exemplary environment for auto-populating pharmacy SIG codes and calculating confidence values in accordance with embodiments of the present disclosure.

FIG. 1 is a block diagram of an exemplary environment for auto-populating pharmacy SIG codes and calculating confidence values in accordance with embodiments of the present disclosure. The environment 100 can include data sources 110 and a pharmacy system 120.

The data sources 110 can include a repository or database of one or more prescriptions 112. The data sources 110 can store prescriptions 112 in, for example, XML-files. The system 120 can interface with the data sources 110 to autonomously auto-populate prescriptions with pharmacy SIG codes for the prescriptions 112 provided from the data sources 110.

The system 120 can include a pattern matching model 130, a pharmacy SIG code generator 140, a confidence value calculator 150, and a pharmacy computing system 160. The system 120 can further include pattern matching model dictionaries 170. The system 120 can generate training data 102 based on a subset of the prescription 112 from the data sources 110.

To train the pattern matching model 130, the training data 102 can be input to the pattern matching model 130 with specified SIG codes, and utilized to build the pattern matching model dictionaries 170 and rules of the pattern matching model 130. Regular expressions (Regex) pattern matching can be used by the pattern matching model 130 for mapping the pattern matching model dictionaries 170. Various rules can be created by the pattern matching model 130 to extract information from prescriptions with regular expressions, which will be described in FIG. 6 below.

In operation, after the pattern matching model 130 has been trained, the prescriptions 112 can be provided from the data sources 110 to the pattern matching model 130. The pattern matching model 130 can parse the unstructured or natural language text of the prescriptions 112 to generate one or more tokens and map each of the tokens to a token SIG using the pattern matching model dictionaries 170. The SIG code generator 140 can generate a prescription SIG code 142 based on each of the token SIG corresponding to each of the tokens. The confidence value calculator 150 can calculate the confidence value of the generated prescription SIG codes as a real-time accuracy measure.

The pharmacy system 120 can include a network of one or more servers and client devices that operate to facilitate conversion of prescriptions by one or more pharmacies. Pharmacists or pharmacy employees can interact with the pharmacy computing system 160 via the client devices. In exemplary embodiments, the generated SIG codes and the calculated confidence values can be output to the computing system 160, and can also be submitted to the pattern matching model dictionaries 170 to update the dictionaries to further train the model.

Figure 2:
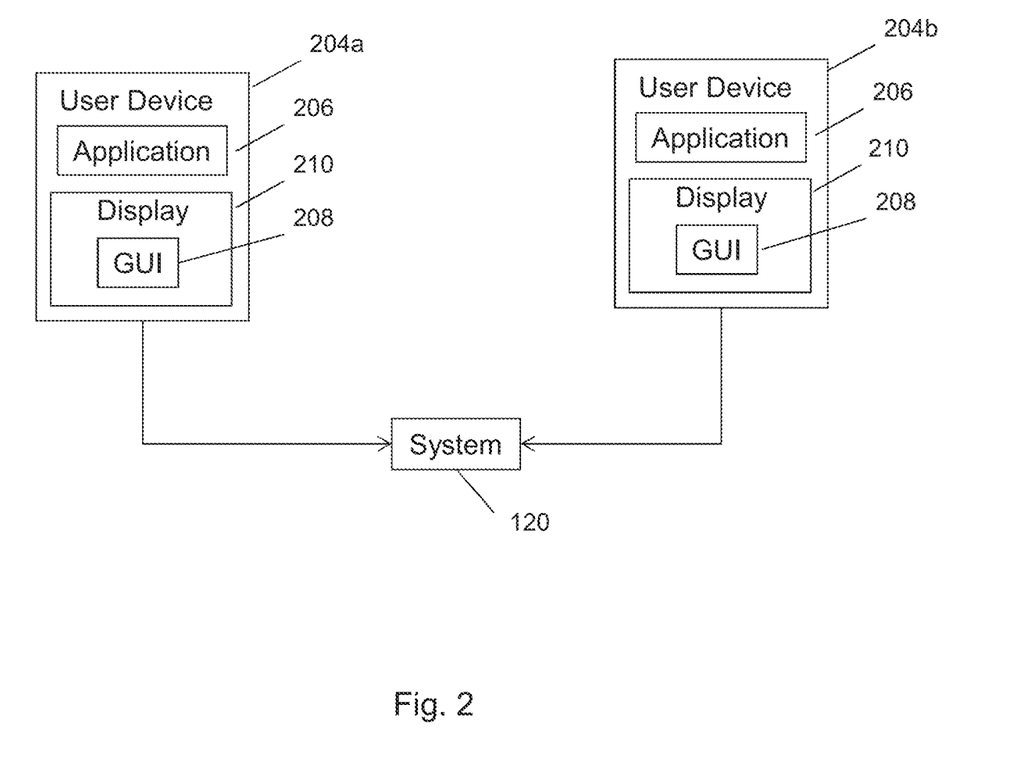
FIG. 2 is a block diagram depicting an embodiment of the pharmacy SIG codes auto-populating system in accordance with exemplary embodiments of the present disclosure.

FIG. 2 is a block diagram depicting an embodiment of the system 120 in accordance with exemplary embodiments of the present disclosure. In exemplary embodiments, the system 120 can be implemented by one or more servers and one or more data repositories, which can communicate directly with each other and/or can communicate with each other via one or more communication networks as described herein. In some embodiments, client devices 204a-b can interact with the system 120. The client devices 204a-b can be computing devices (including a personal computer, a workstation, a tablet, a smart phone, a laptop, a server, and the like) configured to communicate with the system 120 over one or more communication networks using one or more communication protocols.

The client devices 204a-b can each include an application 206, such as a web browser or a stand-alone application specific to the system 120. The application 206 can be downloaded, installed, and executed by the client devices 204a-b (e.g., by a processing device) to interact with the system 120 and/or to render one or more graphical user interfaces (GUIs) 208 associated with the system 120 on a display device 210 of the client devices 204a-b in response to, for example, data and/or instructions received from the system 120. The GUIs 208 rendered on the display device 210 can include data entry areas to receive information from users; can include user-selectable elements or areas that can be selected by the users to cause the system 120 to perform one or more operations, functions, and/or processes; and/or can include data outputs to display information to users. In exemplary embodiments, the GUIs 208 can enable navigation of the system 120. Users can interact with the client devices 204a-b via the GUIs 208 to review the SIG codes generated by the system 120.

Figure 3:
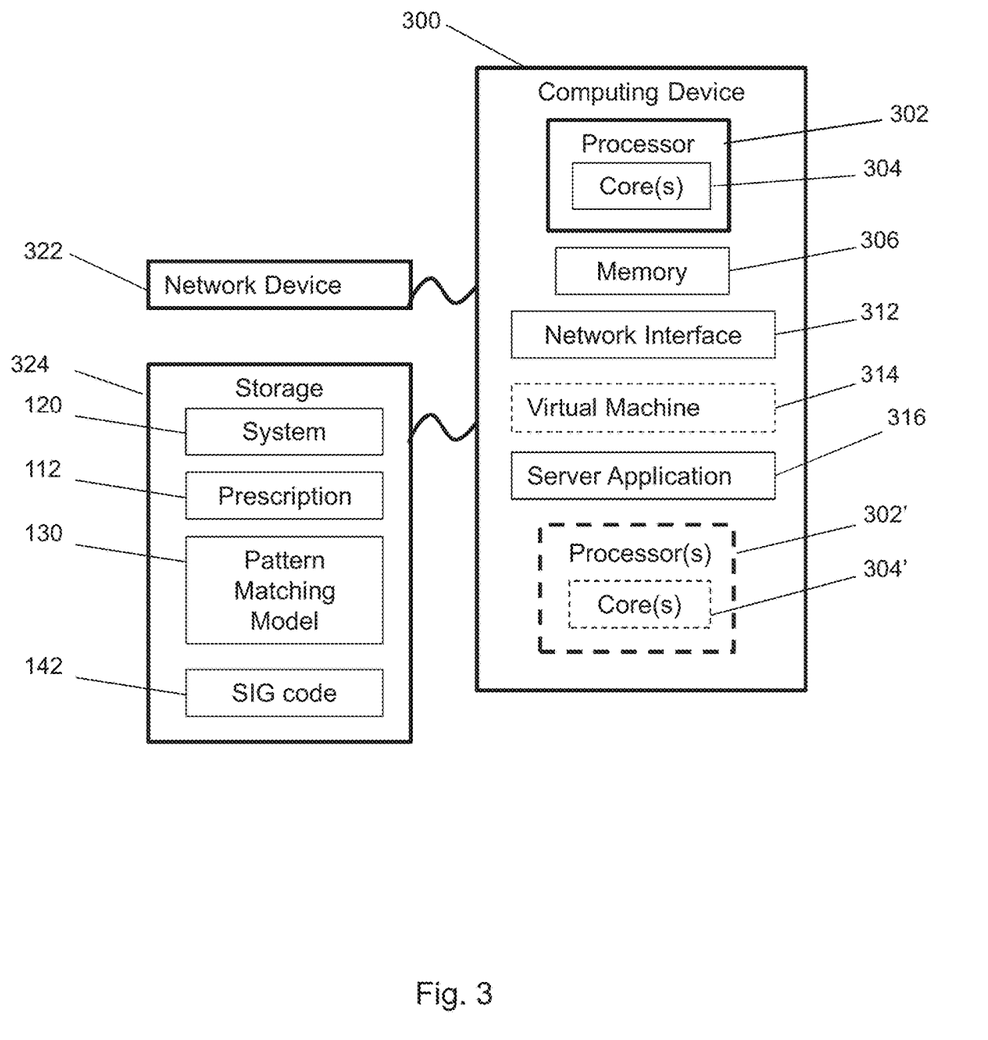
FIG. 3 depicts a block diagram of an exemplary computing device in accordance with embodiments of the present disclosure.

FIG. 3 depicts a block diagram of an exemplary computing device 300 that can be utilized to implement one or more components of an embodiment of the system 120. In exemplary embodiments, the computing device 300 can be implemented as a server. The computing device 300 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 306 included in the computing device 300 may store computer-readable and computer-executable instructions or software for implementing exemplary embodiments of the system 120 or portions thereof. The computing device 300 also includes configurable and/or programmable processor 302 and associated core 304, and optionally, one or more additional configurable and/or programmable processor(s) 302' and associated core(s) 304' (for example, in the case of computer systems having multiple processors/cores), for executing computer-readable and computer-executable instructions or software stored in the memory 306 and other programs for controlling system hardware. Processor 302 and processor(s) 302' may each be a single core processor or multiple core (304 and 304') processor.

Virtualization may be employed in the computing device 300 so that infrastructure and resources in the computing device may be shared dynamically. A virtual machine 314 may be provided to handle a process running on multiple processors so that the process appears to be using only one computing resource rather than multiple computing resources. Multiple virtual machines may also be used with one processor.

Memory 306 may include a computer system memory or random access memory, such as DRAM, SRAM, EDO RAM, and the like. Memory 306 may include other types of memory as well, or combinations thereof.

The computing device 300 may also include one or more storage devices 324, such as a hard-drive, CD-ROM, mass storage flash drive, or other computer readable media, for storing data and computer-readable instructions and/or software that can be executed by the processing device 302 to implement exemplary embodiments of the system 120 described herein. For example, the storage devices can store prescriptions 112, pattern matching model 130, and SIG code 142.

The computing device 300 can include a network interface 312 configured to interface via one or more network devices 322 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections (including via cellular base stations), controller area network (CAN), or some combination of any or all of the above. The network interface 312 may include a built-in network adapter, network interface card, PCMCIA network card, card bus network adapter, wireless network adapter, USB network adapter, modem or any other device suitable for interfacing the computing device 300 to any type of network capable of communication and performing the operations described herein. While the computing device 300 depicted in FIG. 3 is implemented as a server, exemplary embodiments of the computing device 300 can be any computer system, such as a workstation, desktop computer or other form of computing or telecommunications device that is capable of communication with other devices either by wireless communication or wired communication and that has sufficient processor power and memory capacity to perform the operations described herein.

The computing device 300 may run any server application 316, such as any of the versions of server applications including any Unix-based server applications, Linux-based server application, any proprietary server applications, or any other server applications capable of running on the computing device 300 and performing the operations described herein. An example of a server application that can run on the computing device includes the Apache server application.

Figure 4:
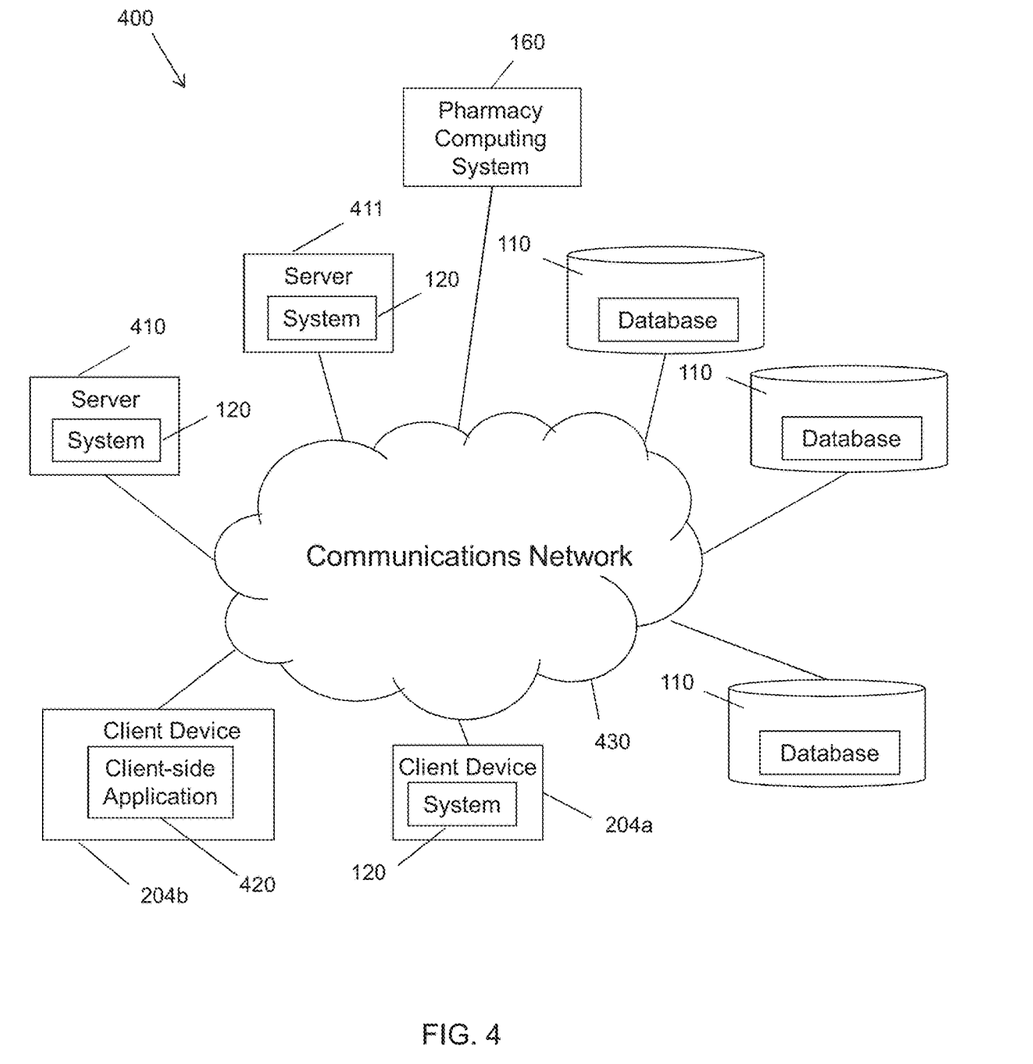
FIG. 4 depicts an exemplary network environment in accordance with embodiments of the present disclosure.

FIG. 4 depicts an exemplary network environment 400 for implementing instances of embodiments of the environment 100 and/or the system 120 or portions thereof in accordance with embodiments of the present disclosure. As shown in FIG. 4, the environment 400 can include servers 410-411, client device 204a-b, and repositories (or databases) 110, which can be operatively coupled to each other via a communication network 430. The communication network 430 can be implemented as an Intranet, virtual private network (VPN), wide area network (WAN), local area network (LAN), and/or other suitable communication network.

Any one of the servers 410-411 can be programmed to implement one or more components of the system 120 or portions thereof including embodiments of the pattern matching model 130, the pharmacy SIG code generator 140, the confidence value calculator 150, and the user interface shown in FIG. 1. In some embodiments, particular servers can be programmed to implement particular portions of the system 120 such that the group of server is collectively programmed to implement embodiments of the system 120 (e.g., the server 410 can execute instances of the pattern matching model 130, and the server 411 can implement instances of the pharmacy SIG code generator 140). In the present example, the server 410 can execute the user interface to facilitate interaction between client devices 204 and the instances of the system 120. The server 411 can receive prescriptions to be processed by the system and can execute the pattern matching model 130 to analyze the prescriptions, execute the SIG code generator 140 to generate the SIG codes, and execute the confidence value calculator 150 to calculate the confidence of the generated SIG codes.

The client devices 204*a*-*b* can be operatively coupled to the severs 410-411 via the communication network 430 to interface with the system 120 to facilitate input of information to the servers 410-411 and review of output from the system 120. In some embodiments, the client devices 204*a*-*b* can implement the system 120 or portion thereof and/or can implement a client side application 420 (e.g., an application specific to the system 120 or a web browser) for interfacing the servers 410-411.

Figure 5:
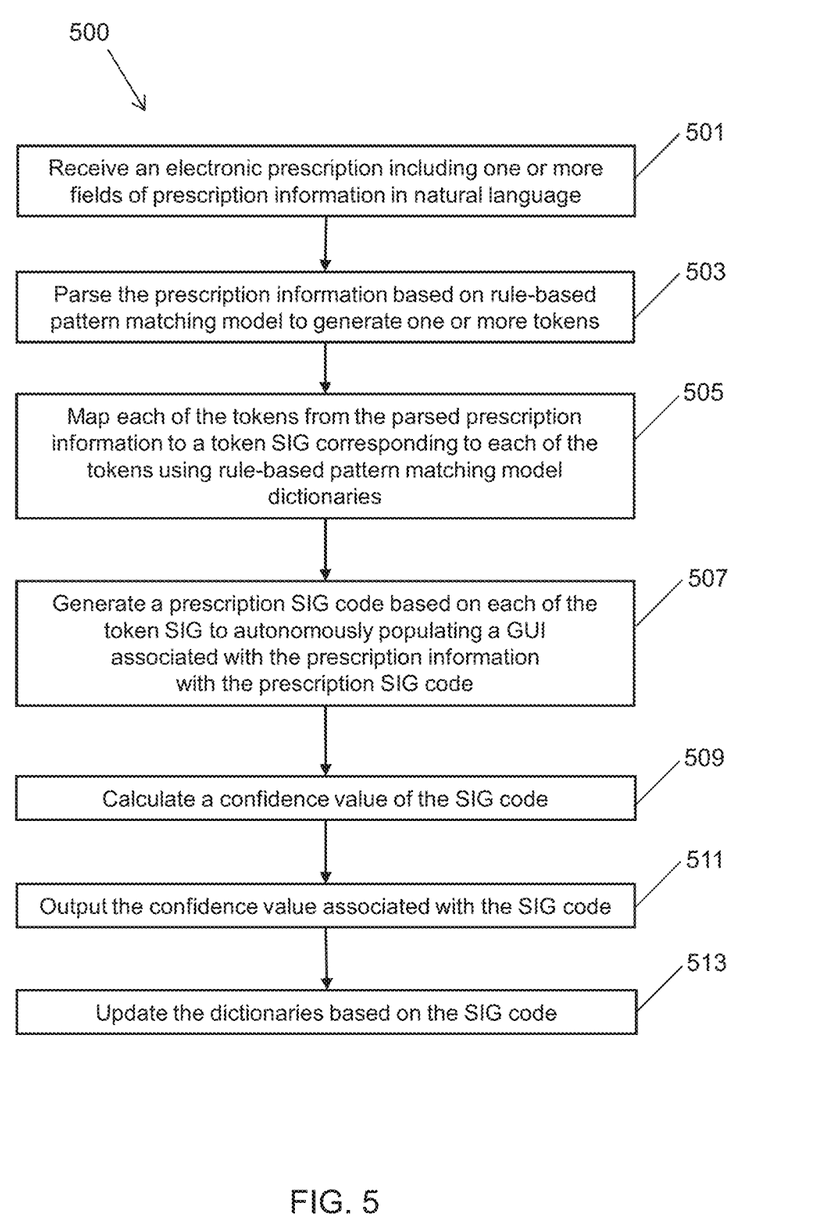
FIG. 5 is a flowchart illustrating an exemplary process for auto-populating pharmacy SIG codes and calculating confidence values in accordance with embodiments of the present disclosure.

FIG. 5 is a flowchart illustrating an exemplary process 500 in accordance with embodiments of the present disclosure. At operation 501, an electronic prescription including one or more fields of prescription information in unstructured or natural language can be received by an embodiment of the pattern matching model of the pharmacy system. In some embodiments, the rule-based pattern matching model can be the regular expressions pattern matching model. The one or more fields of prescription information can be unstructured or in natural language and can include dosage, frequency, add-on, route, duration, verb, and medical conditions. For example, a prescription received by the pattern matching model can be "Take 2 tablet by mouth three times daily for allergy for 30 days".

At operation 503, the prescription information is parsed and tokenized according to the rule-based pattern matching model. The rule-based pattern matching model can extract structured information from the unstructured prescription as different components to form the tokens. For example, in the above mentioned prescription "Take 2 tablet by mouth three times daily for allergy for 30 days", the prescription information is extracted as follows:

the word "take" is extracted as component "verb",
the number "2" is extracted as component "quantity",
the words "tablet" is extracted as component "form",
the words "by mouth" are extracted as component "route",
the words "three times daily" are extracted as component "frequency",
the words "for allergy" are extracted as component "medical condition",
the words "for 30 days" are extracted as component "duration".

At operation 505, the parsed and tokenized prescription information can be mapped to a token SIG corresponding to the parsed and tokenized prescription information based on rule-based pattern matching model dictionaries. In some embodiments, for each component, dictionaries can be created for each field of prescription information to map patterns to the relevant SIG code. For example, if the prescription includes [Digit] {Tablet/Capsule/Drop . . . }, the model can convert the relevant [Digit] to dosage value.

Some components are included to bring in standardization, such as patterns of {max daily dose/max amount per day . . . } [Digit] in the prescriptions can be mapped to MAX[Digit]PD and dosages is milliliters and teaspoons are converted to [Digit]ML format. More exemplary rules to map prescription information with regular expression will be described in FIG. 6 below.

Figure 6:
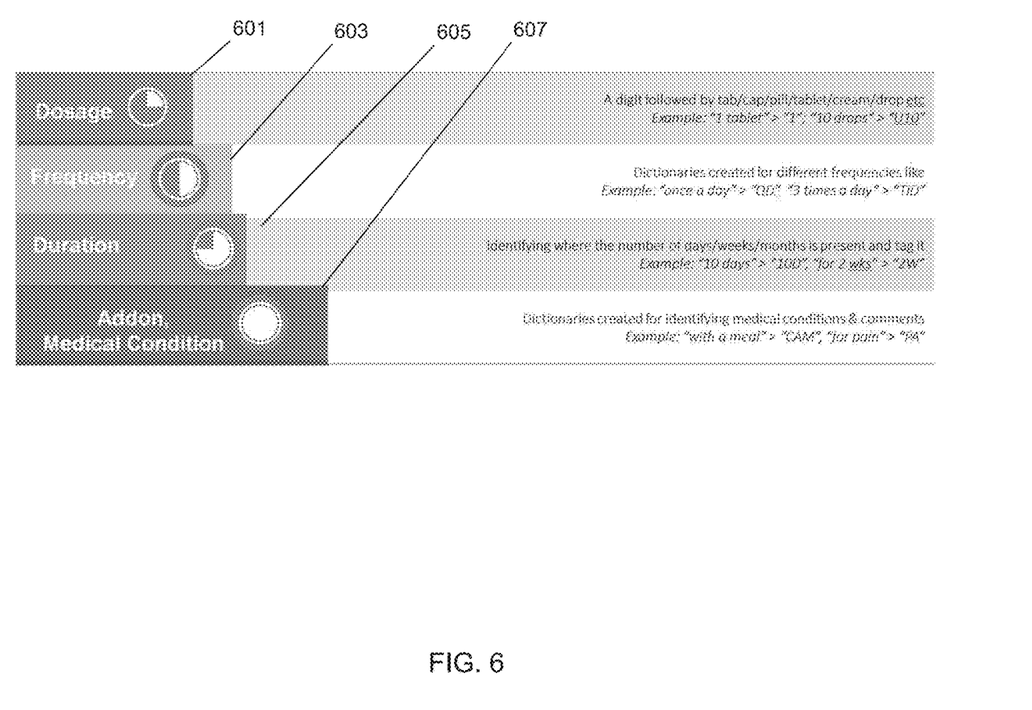
FIG. 6 illustrates exemplary rules to map prescription information with regular expression in accordance with embodiments of the present disclosure.

FIG. 6 illustrates exemplary rules to mapping prescription information with regular expression in accordance with embodiments of the present disclosure. In the prescriptions, usually dosage information includes a digit followed by tab, cap, pill, tablet, cream, or drop, etc. Thus, according to the rules shown in FIG. 6, as for the component 601 "dosage", for example, dosage information "1 tablet" can be converted as SIG code "1", and dosage information "10 drops" can be converted as SIG code "U10".

As for frequency component 603 in the prescriptions, dictionaries are created for different frequency information. For example, according to the rules shown in FIG. 6, frequency information "once a day" can be mapped to SIG code "QD", and frequency information "3 times a day" can be mapped to SIG code "TID".

As for duration component 605 in the prescriptions, the model can identify where the number of days, weeks, or months is present and tag the number. According to the rules shown in FIG. 6, for example, duration information "10 days" can be mapped to SIG code "10D", and duration information "for 2 wks" can be mapped to SIG code "2W".

As for add-on and medical condition components 607 in the prescriptions, dictionaries are created for identifying medical condition and add-on comments. For example, according to the rules shown in FIG. 6, add-on information "with a meal" can be mapped to SIG code "CAM", and medical condition information "for pain" can be mapped to SIG code "PA".

At operation 507, the SIG code generator can generate a prescription SIG code based on the mapped prescription information to autonomous auto-populate prescription information with the prescription SIG code, which can be displayed in a GUI. An exemplary generation of the prescription SIG code will be described in FIG. 7 below.

Figure 7:
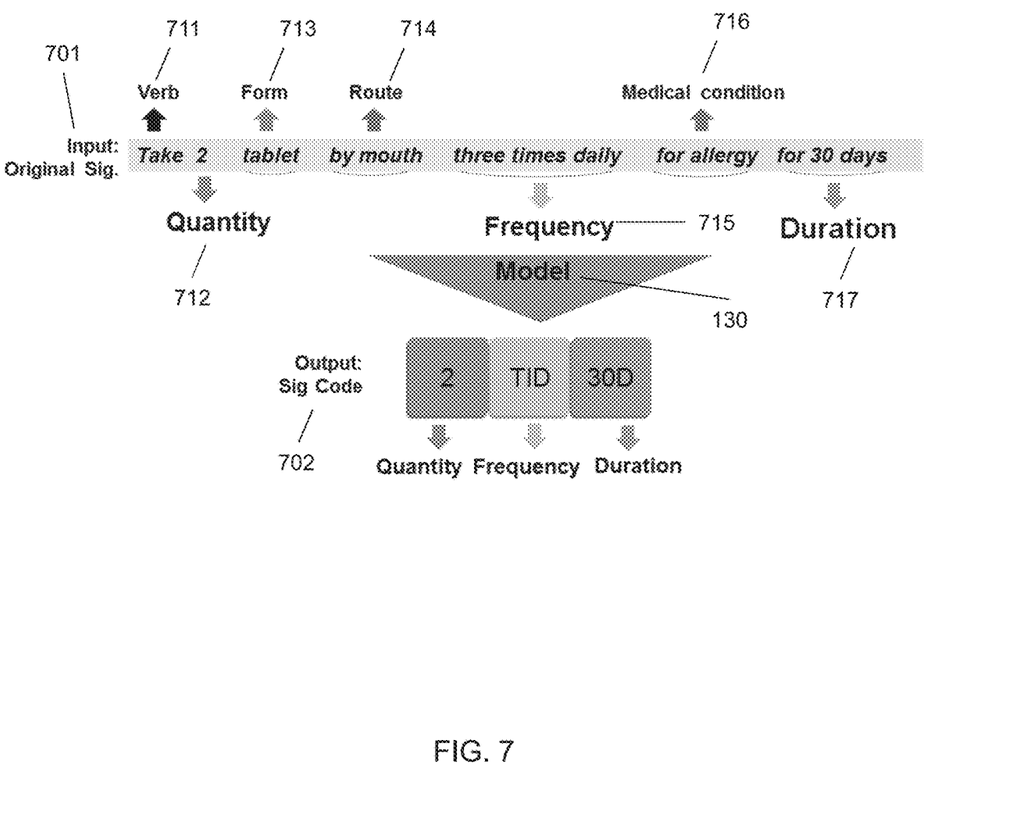
FIG. 7 illustrates an exemplary generation of prescription SIG codes of an electronic prescription in accordance with embodiments of the present disclosure.

FIG. 7 illustrates an exemplary generation of prescription SIC codes of an electronic prescription in accordance with embodiments of the present disclosure. As shown in FIG. 7, for example, the input original signature 701 in the prescription is "Take 2 tablet by mouth three times daily for allergy for 30 days". As described above, the prescription information includes the following components:

component "verb" 711, which is "take",
component "quantity" 712, which is "2",
component "form" 713, which is "tablet",
component "route" 714, which is "by mouth",
component "frequency" 715, which is "three times daily",
component "medical condition" 716, which is "for allergy", and
component "duration" 717, which is "for 30 days".

According to the rules shown in FIG. 6 of the pattern matching model 130, the dosage information "2 tablet", which includes component "quantity" 712 and component "form" 713 can be mapped to token SIG "2"; component "frequency" 715 "three times daily" can be mapped to token SIG "TID"; and component "duration" 717 "30 days" can be mapped to token SIG "30D". Accordingly, output prescription SIG code 702, which is "2TID30D", is generated based on the token SIGs "2", "TID", and "30D".

Referring back to FIG. 5, at operation 509, as a real-time accuracy measure, the confidence value calculator dynamically calculates a confidence value for the generated prescription SIG code based on character coverage of the prescription. The confidence value is calculated as the following equitation:

$$\text{Confidence Value} = \frac{\text{Total number of characters mapped by the rule-based pattern matching dictionaries}}{\text{Total number of characters present in the electronic prescription}} \times 100\%$$

Thus, the confidence value is calculated based on the total number of characters matched by the rule-based pattern matching dictionaries and the total number of characters present in the prescription. Spaces and syntactic characters are excluded from the calculation.

For example, in a prescription "1 capsule (50 MG) QHS.", if the portion "1 capsule QHS" can be mapped by the pattern matching model, the total number of the words in the prescription is 15 (excluding spaces and syntax), the total number of the mapped characters is 11 ('1', 'capsule', and 'QHS'), and there are four characters missed ('50 MG'), and three excluded syntactic characters (characters '(', ')' and '.'). Thus, the confidence score for this prescription will be calculated as:

$$\text{Confidence Value} = \frac{11}{15} \times 100 = 73\% \text{ (roundoff to a whole number)}$$

As another example, for a prescription "Take 1 tab five times daily for 5 days", which contains 30 characters (excluding spaces), all of the 30 characters are mapped by the pattern matching model, and the confidence score for this prescription will be calculated as:

$$\text{Confidence Value} = \frac{30}{30} \times 100 = 100\%$$

As another example, when a prescription "Take 1 tab five times daily for 5 days for suppression", which contains 44 characters (excluding spaces), is mapped by the by the pattern matching model, if only 30 characters are mapped and the words "for suppression" is not mapped, the confidence score for this prescription will be calculated as:

$$\text{Confidence Value} = \frac{30}{44} \times 100 = 68\% \text{ (roundoff to a whole number)}$$

As shown in FIG. 5, at operation 511, the confidence value associated with the SIG code can be output to a pharmacy computing system. The confidence value can indicate an action to be taken associated with the SIG code by a healthcare professional. For example, the confidence value can help the pharmacist to look into parts of the prescription not captured by the pattern matching model, thereby avoiding any lapse in conveying information, and reducing labor cost and improving customer service. Furthermore, the pattern matching model can be specified to incorporate SIG codes for complex instructions, special SIG codes and multiple instruction prescriptions.

At operation 513, the rule-based pattern matching model dictionaries can be updated based on the generated SIG code to further train the model.

In some embodiments, the regular expressions pattern matching model can be trained using a set of training data including a random set of prescriptions. To train the pattern matching model, the random set of prescriptions is utilized to build the dictionaries and rules. The SIG code for each prescription is tokenized and/or normalized to serve as ground truth on which to build the model.

Figure 9:
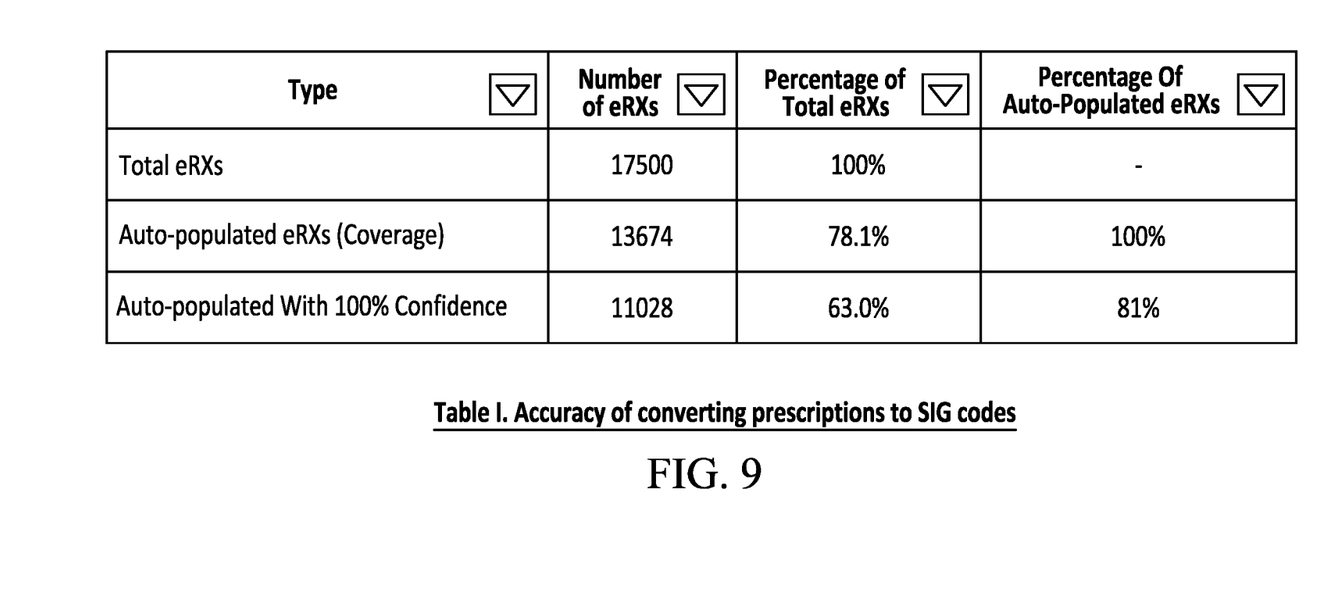
FIG. 9 is a table showing the accuracy of converting prescriptions to SIG codes according to an exemplary embodiment of the present disclosure.

In accordance with embodiments of the present disclosure, Table I as shown in FIG. 9 indicates accuracy of converting prescriptions to SIG codes when a total number of 17,500 electronic prescriptions are input to the pharmacy system. Among the 17,500 electronic prescriptions, 13,674 prescriptions can be auto-populated with the SIG codes, which is 78.1% of the total number of the prescription. Among the 13,674 prescriptions with auto-populated SIG codes, 11,028 prescriptions have SIG codes generated with 100% confidence value. In other words, 63% of the total number of the prescriptions (17,500), or 81% of the number of prescriptions with auto-populated are SIG codes (13,674), have SIG codes generated with 100% confidence value, and there is no need for the pharmacist to recheck these generated SIG codes.

Figure 10:
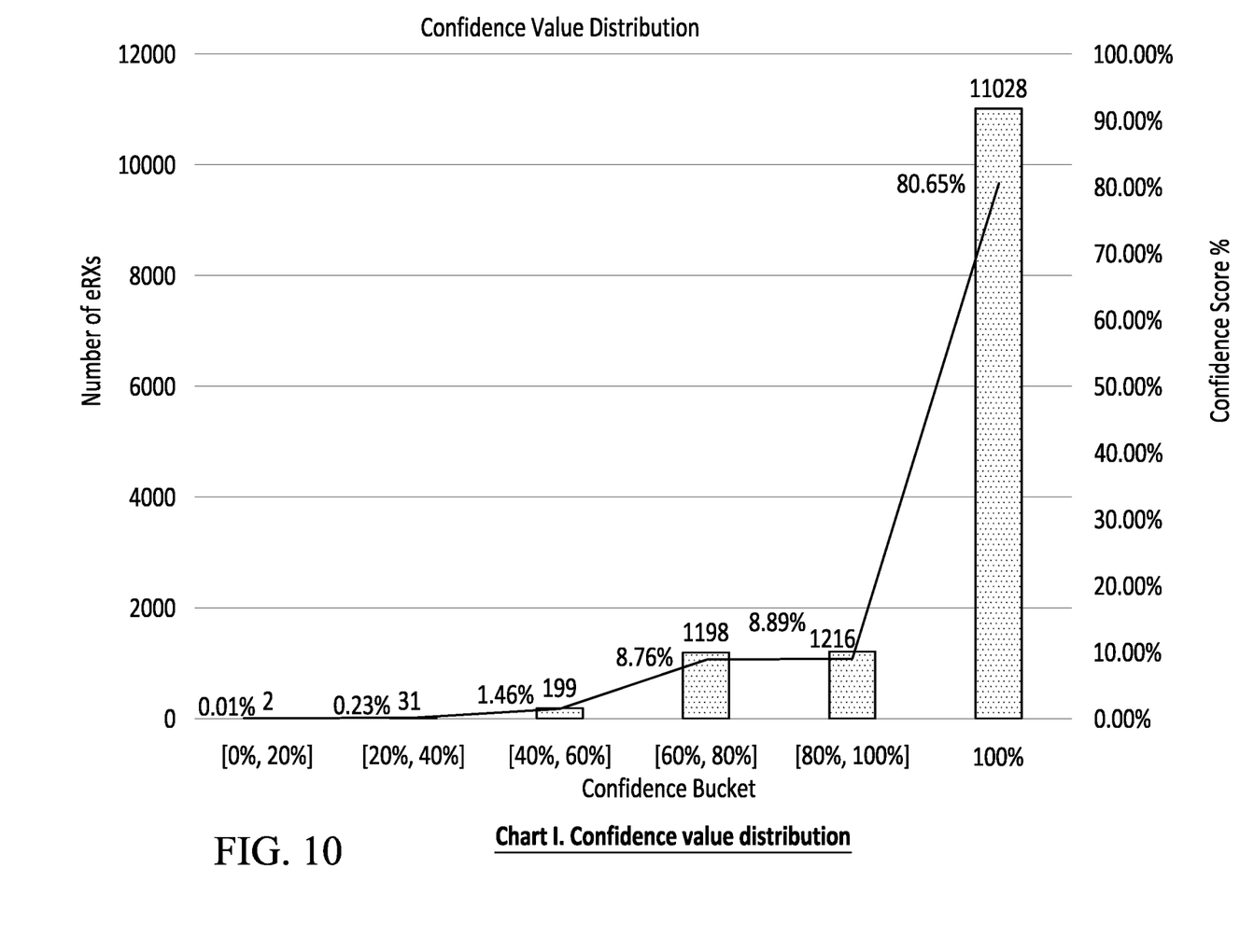
FIG. 10 is a chart depicting the confidence value distribution according to an exemplary embodiment of the present disclosure.
Figure 11:
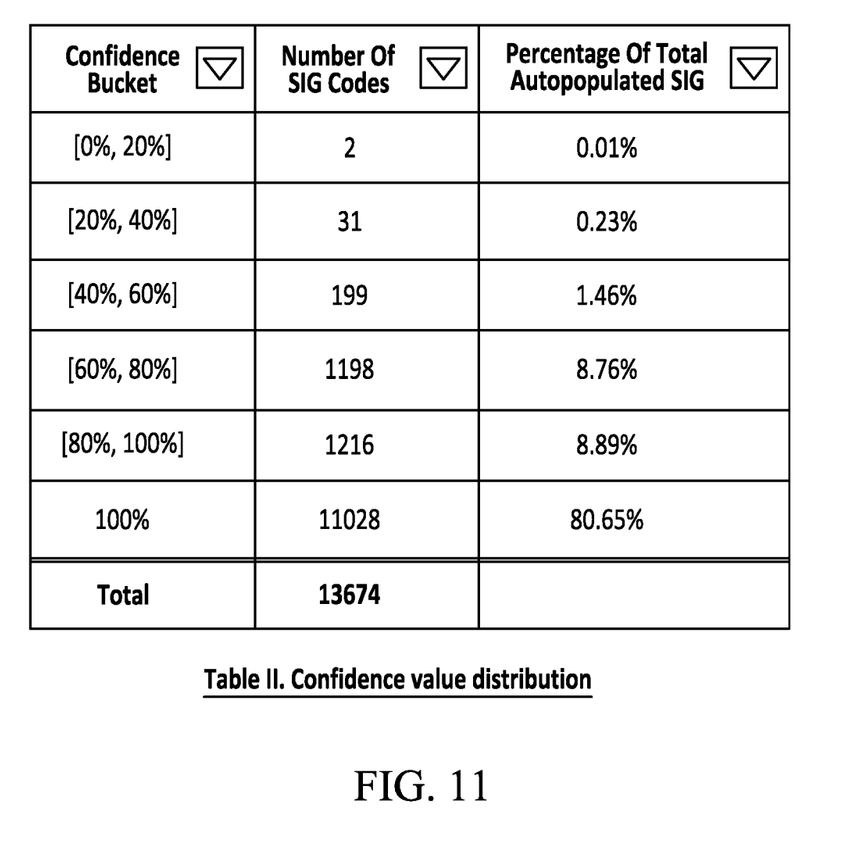
FIG. 11 is a table showing the confidence value distribution according to an exemplary embodiment of the present disclosure.

Further, Chart I as shown in FIG. 10 and Table II as shown in FIG. 11 further indicates the confidence value distribution of the 13,674 prescriptions with auto-populated SIG codes. Among the 13,674 prescriptions with auto-populated SIG codes:

11,028 prescriptions, which is 80.65% of the total number of auto-populated prescription, have SIG codes generated with 100% confidence value;
 1,216 prescriptions, which is 8.89% of the total number of auto-populated prescription, have SIG codes generated with confidence value in the range between 80%-100%;
 1,198 prescriptions, which is 8.76% of the total number of auto-populated prescription, have SIG codes generated with confidence value in the range between 60%-80%;
 199 prescriptions, which is 1.46% of the total number of auto-populated prescription, have SIG codes generated with confidence value in the range between 40%-60%;
 31 prescriptions, which is 0.23% of the total number of auto-populated prescription, have SIG codes generated with confidence value in the range between 20%-40%;
 2 prescriptions, which is 0.01% of the total number of auto-populated prescription, have SIG codes generated with confidence value in the range between 0%-20%.

Accordingly, in accordance with embodiments of the present disclosure, SIG codes related to the electronic prescriptions can be auto-populated with high accuracy.

Figure 8:
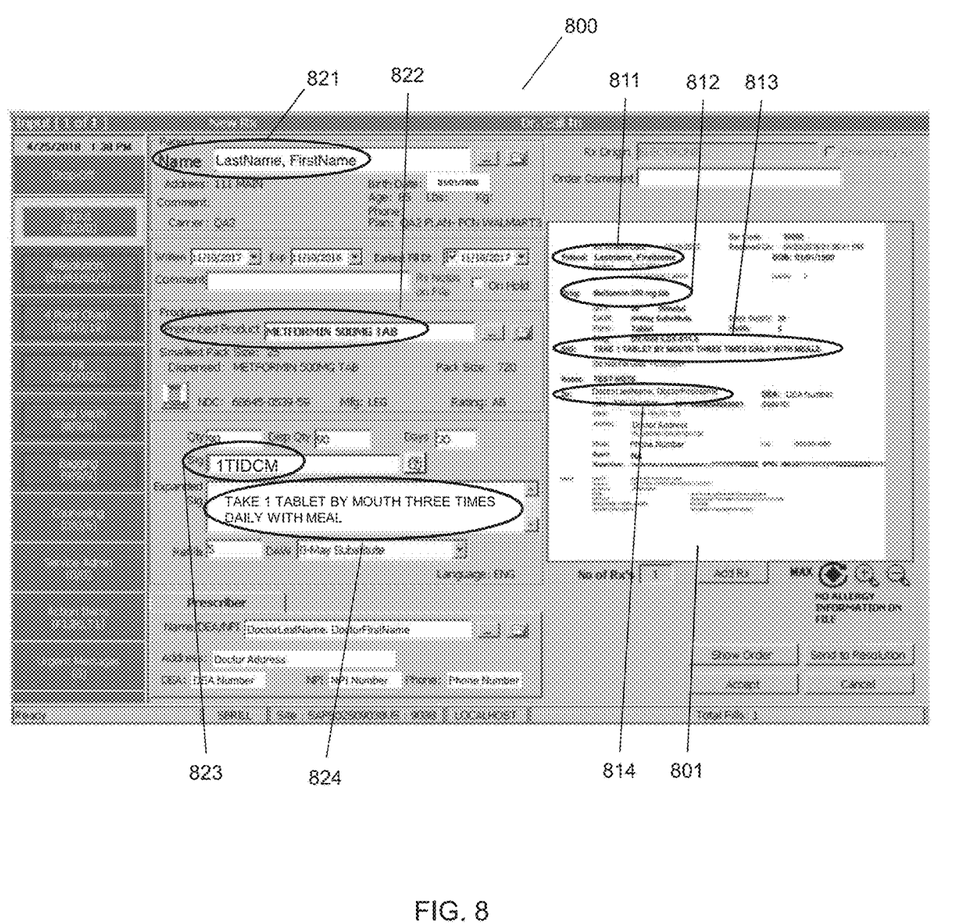
FIG. 8 is a graphical user interface (GUI) of a database for auto-populating prescription SIG codes according to an exemplary embodiment of the present disclosure.

FIG. 8 is a graphical user interfaces (GUI) 800 of a database for auto-populating pharmacy SIG codes in a pharmacy system according to an exemplary embodiment of the present disclosure. As shown in FIG. 8, an electronic prescription 801 can be uploaded into the pharmacy system. The electronic prescription 801 includes patient name 811, drug name 812, signature (i.e., patient instruction) 813, and prescriber name 814. The pharmacy system can extract patient name 811 "LastName, FirstName" from the electronic prescription and enter this information to InputBox 821 "Name". Similarly, drug name 812 "Metformin 500 MG TAB", can be extracted and entered to InputBox 822 "Prescribed Product", and prescriber name 814 "DoctorLastName, DoctorFirstName" can be extracted and entered to InputBox 824 "Prescriber Name/DEA/NPI". The signature 813, "Take 1 tablet by mouth three times daily with meal"

can be extracted, and auto-populated as SIG code "1TIDCM" according to the rules shown in FIG. 6, and then entered to InputBox 823 "SIG". Thus, the prescription information in the electronic prescription can be auto-populated and auto-extracted into the graphical user interfaces (GUI) 800 of the pharmacy system.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The foregoing description of the specific embodiments of the subject matter disclosed herein has been presented for purposes of illustration and description and is not intended to limit the scope of the subject matter set forth herein. It is fully contemplated that other various embodiments, modifications and applications will become apparent to those of ordinary skill in the art from the foregoing description and accompanying drawings. Thus, such other embodiments, modifications, and applications are intended to fall within the scope of the following appended claims. Further, those of ordinary skill in the art will appreciate that the embodiments, modifications, and applications that have been described herein are in the context of particular environment, and the subject matter set forth herein is not limited thereto, but can be beneficially applied in any number of other manners, environments and purposes. Accordingly, the claims set forth below should be construed in view of the full breadth and spirit of the novel features and techniques as disclosed herein.

The invention claimed is:

1. A method of auto-populating pharmacy SIG codes in a pharmacy system, the method comprising:
   receiving an electronic prescription including one or more fields of prescription information in natural language;
   parsing, by a processing device, the one or more fields of prescription information according to rule-based pattern matching model to identify one or more tokens;
   mapping, by the processing device, each of the identified one or more tokens to a token SIG corresponding to each of the identified one or more tokens using rule-based pattern matching model dictionaries;
   combining, by the processing device, each token SIG to generate a prescription SIG code, wherein the prescription SIG code is separate from the electronic prescription; and
   autonomously auto-populating a graphical user interface associated with the prescription information with the prescription SIG code;
   calculating, by the processing device, a confidence value of the prescription SIG code based on character coverage of the electronic prescription, and
   outputting, by the processing device, the confidence value associated with the prescription SIG code, wherein the confidence value is calculated as a function of a number of characters mapped by the rule-based pattern matching model dictionaries and a number of characters present in the electronic prescription.

2. The method of claim 1, wherein the confidence value indicates an action to be taken with the prescription SIG code by a healthcare professional.

3. The method of claim 1, wherein the confidence value is calculated as:

$$\text{Confidence Value} = \frac{\text{Total number of characters mapped by the rule-based pattern matching model dictionaries}}{\text{Total number of characters present in the electronic prescription}} \times 100\%$$

4. The method of claim 1, wherein the one or more fields of prescription information includes dosage, frequency, add-on, route, duration, verb, and medical conditions.

5. The method of claim 1, wherein the rule-based pattern matching model is a regular expressions pattern matching model.

6. The method of claim 5, further comprising:
   training the regular expressions pattern matching model using a set of training data.

7. The method of claim 1, further comprising:
   creating dictionaries for each of the one or more fields of prescription information, and
   updating the dictionaries based on the prescription SIG code.

8. A non-transitory computer-readable medium storing instructions, wherein execution of the instructions by a processing device causes the processing device to implement a method of auto-populating pharmacy SIG codes in a pharmacy system, the method comprising:
   receiving an electronic prescription including one or more fields of prescription information in natural language;
   parsing, by the processing device, the one or more fields of prescription information according to rule-based pattern matching model to identify one or more tokens;
   mapping, by the processing device, each of the identified one or more tokens using rule-based pattern matching model dictionaries to a token SIG corresponding to each of the identified one or more tokens;
   combining, by the processing device, each token SIG to generate a prescription SIG code, wherein the prescription SIG code is separate from the electronic prescription; and
   autonomously, by the processing device, auto-populating a graphical user interface associated with the prescription information with the prescription SIG code;
   calculating, by the processing device, a confidence value of the prescription SIG code based on character coverage of the electronic prescription, and
   outputting, by the processing device, the confidence value associated with the prescription SIG code, wherein the confidence value is calculated as a function of a number of characters mapped by the rule-based pattern matching model dictionaries and a number of characters present in the electronic prescription.

9. The medium of claim 8, wherein the confidence value indicates an action to be taken with the prescription SIG code by a healthcare professional.

10. The medium of claim 8, wherein the confidence value is calculated as:

$$\text{Confidence Score} = \frac{\text{Total number of characters matched by the rule-based pattern matching model dictionaries}}{\text{Total number of characters present in the electronic prescription}} \times 100$$

11. The medium of claim 8, wherein the one or more fields of prescription information includes dosage, frequency, add-on, route, duration, verb, and medical conditions.

12. The medium of claim 8, wherein the rule-based pattern matching model is a regular expressions pattern matching model.

13. The medium of claim 12, wherein execution of the instructions by the processing device
causes the processing device to:
train the regular expressions pattern matching model using a set of training data.

14. The medium of claim 8, wherein execution of the instructions by the processing device
causes the processing device to:
create dictionaries for each of the one or more fields of prescription information, and
update the dictionaries based on the prescription SIG code.

15. A system for auto-populating pharmacy SIG codes in a pharmacy system, the system comprising:
a computer storage device storing rule-based pattern matching model; and
a processing device programmed to execute the rule-based pattern matching model to:
receive an electronic prescription including one or more fields of prescription information in natural language;
parse, by the processing device, the one or more fields of prescription information according to the rule-based pattern matching model to identify one or more tokens;
map, by the processing device, each of the identified one or more tokens using rule-based pattern matching model dictionaries to a token SIG corresponding to each of the identified one or more tokens;
combine, by the processing device, each token SIG to generate a prescription SIG code, wherein the prescription SIG code is separate from the electronic prescription; and
autonomously auto-populate, a graphical user interface associated with the prescription information with the prescription SIG code;
calculate, by the processing device, a confidence value of the prescription SIG code based on character coverage of the electronic prescription, and
output, by the processing device, the confidence value associated with the prescription SIG code, wherein the confidence value is calculated as a function of a number of characters mapped by the rule-based pattern matching model dictionaries and a number of characters present in the electronic prescription.

16. The system of claim 15, wherein the confidence value indicates an action to be taken with the prescription SIG code by a healthcare professional.

17. The system of claim 15, wherein the confidence value is calculated as:

$$\text{Confidence Score} = \frac{\text{Total number of characters matched by the rule-based pattern matching model dictionaries}}{\text{Total number of characters present in the electronic prescription}} \times 100$$

18. The system of claim 15, wherein the one or more fields of prescription information includes dosage, frequency, add-on, route, duration, verb, and medical conditions.

19. The system of claim 15, wherein the rule-based pattern matching model is a regular expressions pattern matching model.

20. The system of claim 19, wherein the processing device is programmed to execute the rule-based pattern matching model to:
train the regular expressions pattern matching model using a set of training data.

21. The system of claim 15, wherein the processing device is programmed to execute the rule-based pattern matching model to:
create dictionaries for each of the one or more fields of prescription information, and
update the dictionaries based on the prescription SIG code.

* * * * *